United States Patent
Schmidt et al.

(10) Patent No.: US 10,952,666 B2
(45) Date of Patent: Mar. 23, 2021

(54) SYSTEM AND METHOD FOR MANAGING NOCTURNAL TREATMENT

(71) Applicant: FRESENIUS MEDICAL CARE HOLDINGS, INC., Waltham, MA (US)

(72) Inventors: Daniel Schmidt, Petaluma, CA (US); Bert D. Egley, Walnut Creek, CA (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 399 days.

(21) Appl. No.: 15/191,945

(22) Filed: Jun. 24, 2016

(65) Prior Publication Data
US 2017/0367646 A1 Dec. 28, 2017

(51) Int. Cl.
| | | |
|---|---|---|
| A61B 5/00 | (2006.01) | |
| A61M 1/16 | (2006.01) | |
| A61M 1/28 | (2006.01) | |
| G16H 40/63 | (2018.01) | |
| G16H 20/17 | (2018.01) | |
| G16H 50/30 | (2018.01) | |

(52) U.S. Cl.
CPC .......... *A61B 5/4839* (2013.01); *A61B 5/4812* (2013.01); *A61B 5/7275* (2013.01); *A61B 5/746* (2013.01); *A61M 1/16* (2013.01); *A61M 1/28* (2013.01); *G16H 20/17* (2018.01); *G16H 40/63* (2018.01); *G16H 50/30* (2018.01); *A61M 1/1601* (2014.02); *A61M 1/282* (2014.02); *A61M 2205/3331* (2013.01); *A61M 2205/3344* (2013.01); *A61M 2205/3375* (2013.01); *A61M 2205/3576* (2013.01); *A61M 2205/42* (2013.01); *A61M 2205/502* (2013.01); *A61M 2230/06* (2013.01); *A61M 2230/10* (2013.01); *A61M 2230/42* (2013.01); *A61M 2230/50* (2013.01); *A61M 2230/63* (2013.01)

(58) Field of Classification Search
None
See application file for complete search history.

(56) References Cited

U.S. PATENT DOCUMENTS

| | | |
|---|---|---|
| 2007/0175827 A1 | 8/2007 | Wariar |
| 2009/0114582 A1 | 5/2009 | Grant et al. |
| 2009/0192556 A1* | 7/2009 | Wu .............. A61B 5/0031 607/3 |
| 2009/0294339 A1 | 12/2009 | Biewer et al. |
| 2011/0082445 A1 | 4/2011 | Van der Helm et al. |

(Continued)

OTHER PUBLICATIONS

International Search Report and the Written Opinion of the International Searching Authority from corresponding PCT/US2017/038938 dated Oct. 30, 2017.

(Continued)

*Primary Examiner* — Lauren P Farrar
*Assistant Examiner* — Hamza A Darb
(74) *Attorney, Agent, or Firm* — Lando & Anastasi, LLP (57) ABSTRACT

Treatment controllers and methods are provided that can be integrated with treatment systems, such as peritoneal dialysis systems, hemodialysis systems, and nocturnal treatment systems, to manage execution of treatment operations or a course of treatment based on timing information and/or patient sleep state.

66 Claims, 5 Drawing Sheets

(56) References Cited

U.S. PATENT DOCUMENTS

| | | | |
|---|---|---|---|
| 2011/0301472 A1* | 12/2011 | Grober | A61B 5/021 600/485 |
| 2013/0184638 A1* | 7/2013 | Scarpaci | A61M 1/166 604/28 |
| 2013/0277306 A1 | 10/2013 | Chapman et al. | |
| 2014/0121845 A1* | 5/2014 | Mueller | A61M 1/14 700/282 |
| 2016/0074618 A1 | 3/2016 | Foote | |

OTHER PUBLICATIONS

Extended European Search Report from corresponding European Application No. 17816266.5 dated Dec. 16, 2019.

* cited by examiner

SYSTEM AND METHOD FOR MANAGING NOCTURNAL TREATMENT

BACKGROUND

Technical Field

The technical field of this disclosure relates to medical devices, and controllers for tailoring treatment execution responsive to optimal patient physiological parameters during sleep cycles.

Background Discussion

Home dialysis treatment, whether for hemodialysis or peritoneal dialysis, is commonly performed at night while a patient sleeps. Both treatment systems require use of electromechanical equipment (e.g., pumps, valves, actuators, switches, latches, and compressors, among other options) to pump a filtrate solution. A frequent problem and/or complaint from patients is directed to the noise generated by their treatment system while running. This problem can be exacerbated as conventional treatment begins just as the patient is attempting to start sleep.

SUMMARY

Broadly stated, various aspects are directed to improved treatments methods and systems (e.g., peritoneal dialysis and hemodialysis systems) that are configured to accommodate patient sleep cycles. Research into sleep disturbances from noise show that humans display varying sensitivity to noise depending on the stage of sleep (sleep cycle). Furthermore, sleep disturbance appears to have a most detrimental impact when occurring shortly after falling asleep or shortly prior to normal awakening. Commonly home dialysis treatment begins as the patient is getting ready to sleep, which could result in sleep disturbance at the most disruptive time. It is realized that targeting treatment execution to when a patient is in their deepest sleep cycle (e.g., deep REM sleep) or delaying treatment until the most sensitive periods have past, improves nocturnal treatment systems. In some embodiments, dialysis treatment systems are particularly suited to improved execution based on accommodating patient sleep cycles.

According to one embodiment, a home treatment system is configured to provide in home dialysis. The home treatment system can be either a home peritoneal or home hemodialysis treatment system. In one embodiment, the home treatment system accepts user input that defines a time for triggering treatment. For example, a patient may specify a specific time for starting treatment via a time component. In another example, the patient may specify a delay period that must expire before treatment commences.

According to another embodiment, the home treatment system can monitor physiological parameters of the patient and control treatment execution responsive to the captured physiological parameters. In one example, the treatments system includes or is connected to a pressure sensor which monitors the pressure of a solution (e.g., dialysate, filtered blood, removed blood, etc.) being delivered to or taken from the patient. The pressure readings from the pressure sensor are analyzed to determine a sleep state of the patient (e.g., derive heart rate from sensor readings and determine sleep state, detect variation in pressure reading (e.g., lower average pressure) indicative of deeper sleep state, etc.). According to one embodiment, a treatment controller can manage the execution, for example, of dialysis treatment. In one example, the controller triggers treatment execution responsive to sensors readings indicating deep sleep. In other embodiments, the controller can project sleep states based on historic data and current readings. The controller can synchronize treatment execution so that the loudest operations occur during deep sleep cycles (e.g., projected deep sleep cycles).

In further embodiments, external sensors and/or sensor subsystems can be implemented to generate additional information on a patient's sleep state. Any one or more of heart rate monitors, respiration monitors, wearable sensors, thermal imaging, visual range imaging, audio sensors, etc., can be used to capture information on a patient's sleep state. The captured information can be used by a treatment controller to manage treatment execution/operation of the home treatment system. In some alternative embodiments, addition sensor subsystems (e.g., imaging systems, audio sensors, heart rate monitors, etc.) can be used to capture information on co-sleepers as well as on the patient undergoing treatment. In one embodiment, the treatment controller is configured to manage treatment execution so that both the patient and any co-sleeper are in a deep sleep state during operation of the home treatment system. In further examples, the controller constrains operation of the home treatment system so that the loudest activities occur as one or more sleepers are in their deepest sleep cycles.

Other aspects, embodiments and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Any embodiment disclosed herein may be combined with any other embodiment. References to "an embodiment," "an example," "some embodiments," "some examples," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearances of such terms herein are not necessarily all referring to the same embodiment or example.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

According to one embodiment, a home treatment system is configured to provide in home dialysis. The home treatment system can be either a home peritoneal or home hemodialysis treatment system. In one example, the home treatment system accepts user input that defines a time for triggering treatment. The patient is able to access user interfaces displayed on the treatment device to enter a time period (e.g., a specific time, a time period, countdown period, etc.). The time period input by the user sets a time that the treatment system uses to govern treatment execution (e.g, a specific time for the controller to start treatment, a count-down upon expiration treatment begins, or a time window for treatment to start, etc.). In further examples, the treatment system can incorporate or communicate with manual or electronic timers (e.g., in the dialysis treatment equipment). The timers can be used to delay any execution of a treatment cycle. In other embodiments, remote applications can be used to communicate timing information to the treatment system. For example, the remote application can display graphical user interfaces on a mobile device for entering timing data. In other embodiments, the remote application can track any timing data and communicate a triggering signal to the treatment system.

In other embodiments, timing parameters can be linked to specific functions executed by the treatment system. In some implementations, various functions or treatment operations are associated with noise levels (e.g, decibel readings, approximations, and/or estimation of noise level). The user can instruct the treatment system to delay any of the functions exceeding a user or system specified threshold for noise. The timer could optionally allow the patient to set a treatment start time to some specific time at night or to delay noisier functions in treatment (e.g. operation of compressor or pump, etc.) for some period of time after initiation of treatment.

Another embodiment captures and analyzes information from sensors in communication with the treatment system and/or a treatment controller. An example treatment system can include embedded pressure sensors that monitor pressure at a cassette pump associated with a peritoneal dialysis system (e.g., the Fresenius Liberty™ Cycler and Liberty™ PDx Cycler can include a pressure sensor located on the cassette pump plate inside a machine door—described in greater detail with reference to FIG. 2 below). According to one embodiment, the patient pressure sensor senses pressure inside the patient's peritoneum, and can be used to detect patient biological parameters corresponding to sleep (e.g., lowered heart rate, or lowered respiration rate). In one example, the pressure sensor is used to detect pressure fluctuations triggered by the patient's heart beat or breathing. Likewise, the pressure sensor can detect patient parameters associated with any changes in sleep state, including awakening states (e.g., the pressure sensor can detect increased heart rate, increased respiration, and movement during sleep). Various embodiments can incorporate information from multiple sensors to establish reliable information on the patient's sleep state. For example, patients can be provided heart rate and/or respirations sensors to connect to the treatment system. In another embodiment, the treatment system can connect to a mobile device (e.g., a smart phone, a wearable device, an activity tracking device, a sleep manager, etc.) or other fitness devices and receive sensor data regarding the patient. The sensors from such devices can also provide information on the noise produced by the treatment system. With reliable sleep state information, any operating noise of the treatment system can be synchronized with sleep states where the patient is least sensitive to such noise. For example, if the patient pressure sensor detects a low heart rate and/or low respiration rate associated with a deep sleep state (e.g., as defined by a treatment controller and/or data records for sleep state parameters), the controller can then trigger operation of compressor, pumps, etc., that are used during treatment.

According to another aspect, sensor feedback can also enable additional safety features for home treatment (e.g., dialysis) systems. In one example, safety controls are configured to trigger machine alarms if the patient's biological parameters (e.g., heart rate or respiration rate) reach unsafe levels. In another example, if any of the sensors detect a heart rate is outside a predetermined safe range (e.g., access programmed rates associated with too high or too low heart rates) the system can be configured to alarm and/or stop treatment. Further, the treatment controller could communicate such alarm conditions to emergency medical agencies or personnel (e.g., local hospital, 911, emergency response system, etc.).

Examples of the methods and systems discussed herein are not limited in application to the details of construction and the arrangement of components set forth in the following description or illustrated in the accompanying drawings. The methods and systems are capable of implementation in other embodiments and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Example Treatment Control System

Some embodiments implement a treatment controller for a dialysis treatment system that provides for and can automatically control execution of any treatment function during a course of dialysis treatment. The treatment controller can be configured to manage execution of treatment operations (e.g., activate pump to deliver dialysate to a patient) based on a noise level associated with the treatment operation and/or based on sleep state information associated with the patient. In this manner, the treatment controller provides for more effective treatment, and in particular, treatment execution occurs at times that the patient is least sensitive to noise disturbance in their sleep cycle.

Figure 1:
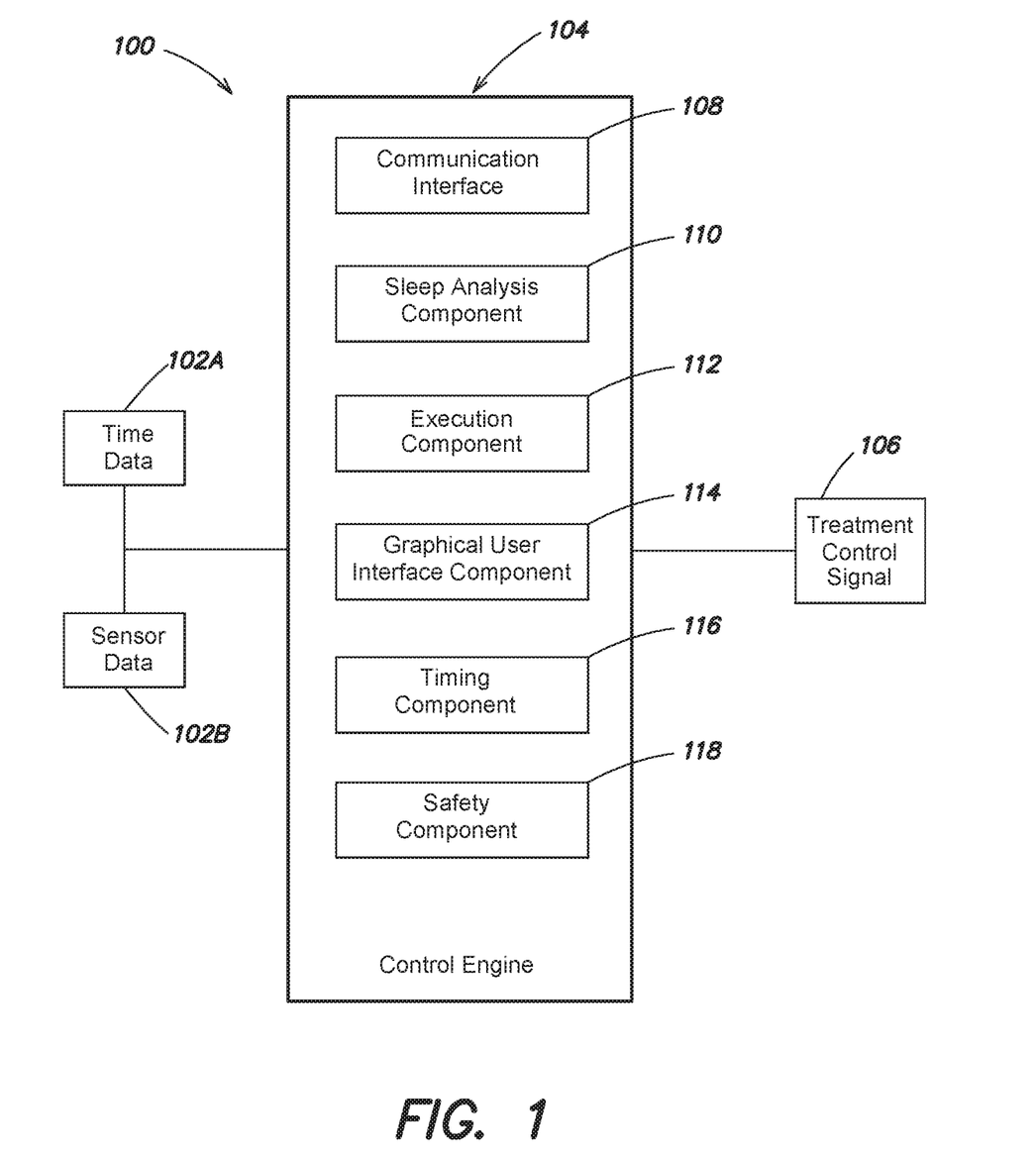
FIG. 1 is a block diagram of an example treatment controller.

FIG. 1 is a block diagram of one embodiment of a treatment controller 100 which may include a control engine 104. The treatment controller 100 and/or engine is configured to access time data 102A and/or sensor data 102B and deliver one or more treatment control signals 106 configured to execute any one or more treatment functions or a course of treatment associated with various treatment systems. The communication between the treatment controller 100 and the treatment system can be bi-directional, whereby the treatment system acknowledges control signals, and/or can provide state information associated with the treatment system and/or requested operations. For example, system state information can include a state associated with specific operations to be executed by the treatment system (e.g., trigger pump to deliver dialysate, trigger pumps and/or compressors to deliver filtered blood, etc.), a status associated with specific operations (e.g., ready to execute, executing, completed, successfully completed, queued for execution, waiting for control signal, etc.).

According to some embodiments, the treatment systems can include hemodialysis systems and peritoneal dialysis systems used to filter contamination or particulates from patient blood. In other embodiments, the treatment controller can be used by other treatment systems. For example, the treatment controller is particularly suited to manage treatment systems that execute overnight and/or during patient sleep cycles (e.g., apnea and/or oxygen therapy systems, muscular stimulation systems, etc.). The treatment controller 100 manages any treatment execution such that the loudest noise levels generated during treatment coincide, to the extent possible subject to other constraints, with deep sleep states or decreased patient sensitivity to noise. For example, the treatment system may include a pump under control of the treatment controller 100. In this example, the treatment controller 100 may preferentially direct the pump to run when the patient is in a deep sleep.

Figure 5:
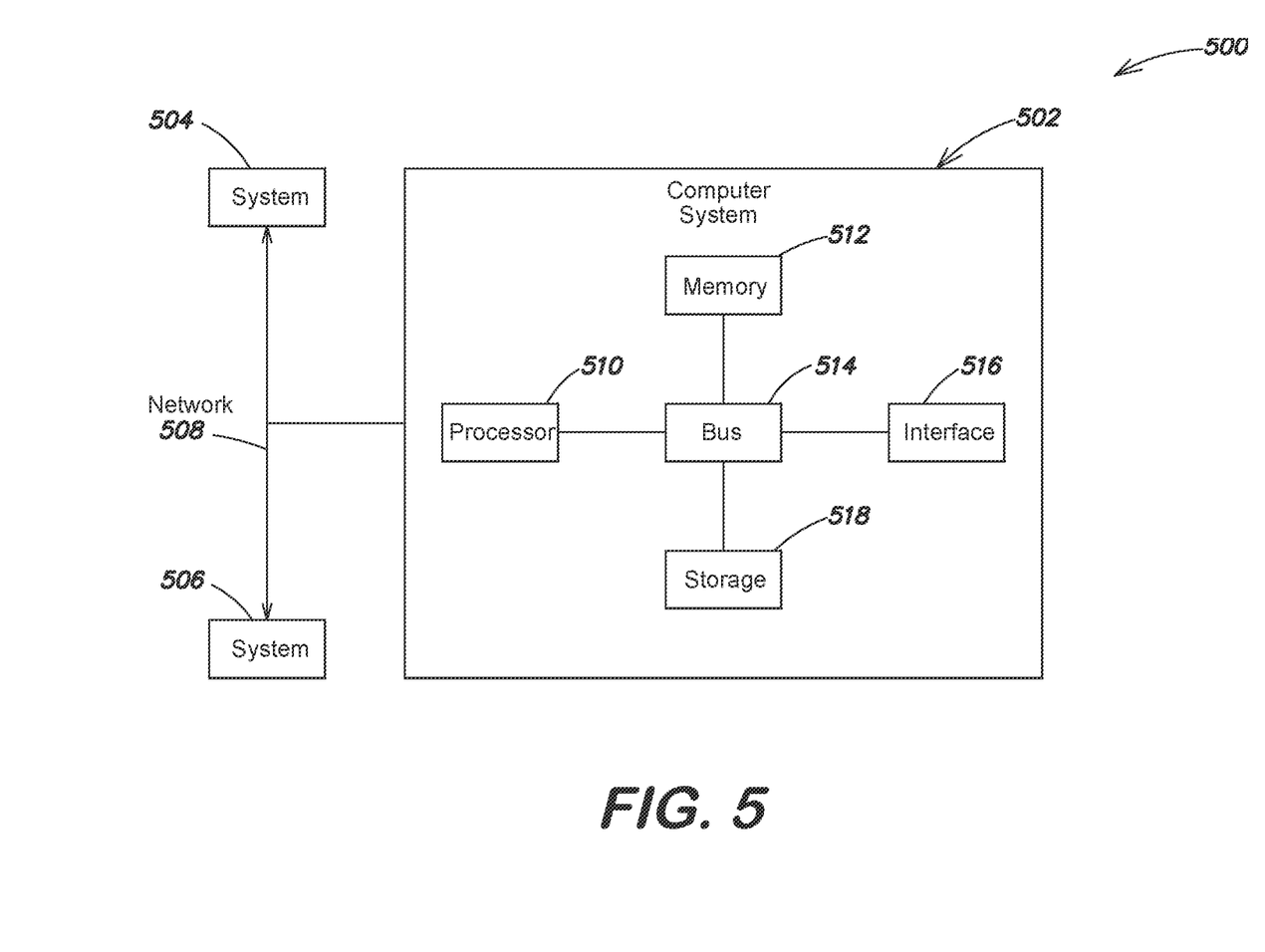
FIG. 5 a schematic diagram of an example implementation of a treatment controller that may be configured to perform processes and functions disclosed herein.

Returning to FIG. 1, the treatment controller 100 and/or control engine 104 can be implemented with a variety of architectures. The treatment controller 500 in FIG. 5 illustrates an example implementation. For example, the controller 100 and/or control engine 104 can be executed on a processor 502 of the treatment controller 500 to provide the functions and operations discussed herein (e.g., monitoring sleep state, generating control signals for treatments systems, scheduling operations for projected deep sleep periods, etc.). It is appreciated that the treatment controller 100 and/or engine 104 can also be implemented in an external system in communication with a treatment system (e.g., hemodialysis or peritoneal dialysis treatment system, among other examples).

As shown in FIG. 1, the treatment controller 100 and/or engine 104 can include specialized components to execute various functions for managing treatment operations or a course of treatment based on patient sleep state and/or noise level. In other embodiments, the treatment controller 100 or control engine 104 can execute any of the functions discussed for any of the system components. In one embodiment, the controller 100 and/or engine 104 can include a communication interface 108 for communicating the control signals to a treatment system or to components of a treatment system. In some embodiments, the communication interface is configured to request sensor data 102B from connected sensors (e.g., pressure sensor for monitoring fluid pressure). The connected sensors can include sensors on other systems. For example, the communication interface 108 can be configured to detect and communicate with mobile devices (e.g., smart phones, web cameras, fitness devices, activity tracking devices, wearable devices, etc.) to obtain sensor data.

The communication interface 108 can request or receive available sensor data and pass the sensor data for analysis to determine a patient sleep state. According to one embodiment, the controller 100 and/or engine 104 includes a sleep analysis component 110. In some examples, the sleep analysis component 110 is configured to compare sensor readings to stored data which can include threshold values or ranges of values for determining stages of sleep. Stages of sleep are defined to include multiple stages (e.g., stage 1—light sleep, stage 2—eye movement stops, stage 3 and/or stage 4 (stage 3 and 4 have been combined is some research)—deep sleep, and rapid eye movement ("REM") sleep, respectively). In some examples, the treatment controller 100 or sleep analysis component can determine a stage of sleep, an in other determines that the patient is in a deep sleep state (e.g., stages 3, 4, or REM sleep). The determination of sleep state can be used by the controller to initiate treatment (e.g., start dialysis treatment at deep sleep state).

In one example, the sleep analysis component 110 determines that the patient's respiration rate has decreased by any one or more of 10%, 15%, and 20% to identify entry into a deep sleep state. In another example, respiration decreases slightly and becomes regular in frequency as sleep progresses until reaching REM sleep. The analysis component 110 can be configured to identify the changes in respiration frequency. In another example, a decrease in heart rate is used to determine entry into a deep sleep state (e.g., reduced heart rate by 5%, 10%, ranges between 5-10% or more). According to one embodiment, a pressure sensor can monitor a fluid pressure (e.g., in the patient's peritoneal cavity) and correlate fluctuations in the fluid pressure with heart rate and/or respiration rate to yield a patient sleep state. In other embodiments, temperature readings, changes in degree in movement in bed, etc., can all be used to identify deep sleep (alone or in combination). Still other techniques to identify a deep sleep state are possible.

Responsive to determining a patient has entered a deep sleep state, the treatment controller 100 and/or engine 104 can be configured to start, for example, a course of dialysis treatment. According to one embodiment, the treatment controller 100 and/or control engine 104 can include an execution component 112 configured to manage treatment operations or a course of treatment responsive to patient sleep state. According to one embodiment, the execution component 112 is configured to delay start of any treatment until the patient is in a deep sleep state or in slow wave sleep. According to another embodiment, the execution component 112 can be configured to schedule treatment operations so that specific functions (e.g., activate pump to delivery fluid, activate compressor, etc.) that produce loud noise occurs at or during deep sleep states.

In further embodiments, the sleep analysis component can be configured to model a patient sleep cycle (e.g., progression through sleep states), and use the model to extrapolate an expected sleep state and time for that sleep state. For example, the sleep analysis component can record sensor readings and timing associated with determined sleep states to build the sleep model. The execution component 112 can schedule treatment operations or start treatment at a time so that operations producing loud noise occur at a time where the patient is expected to be in a deep sleep state. For example, operations that generate noise above a threshold noise level (e.g., 30 decibels (dB), 35 dB, 40 dB, etc.) may be preferentially performed at times when the patient is in REM sleep. In some examples, different thresholds can be set for specific sleep states (e.g., operating volume must be <20-30 dB stage 1, <25-35 dB stage 2, or in the preceding examples for stage 3 & REM sleep). According to another embodiment, the execution component 112 can be configured to adjust noise thresholds responsive to changes in patient sleep state using captured sleep state information. For example, if noise levels above 40 dB trigger awakening or awake sleep states from stage 2, stage 3, or REM state, the respective thresholds can be modified to occur below 40 dB (e.g., 38 dB, 37 dB, 36 dB, etc.). In various examples, the treatment controller 100 and/or the treatment system is configured to learn from prior execution data to identify times most likely to limit sleep disturbance and/or to improve a patient sleep model.

In some embodiments, the treatment controller 100 and or execution component 112 can generate or access an expected course of treatment timeline that establishes sound levels produced at given times, time periods, and/or for specific operations during a course of treatment. The execution component 112 can be configured to manage treatment execution to synchronize modelled sleep states with the treatment timeline and noise levels.

In some implementations, the execution component 112 utilizes predefined noise levels stored in a memory associated with the treatment controller (e.g., a database). The execution component 112 can also use real time sound readings captured by microphones or other audio sensors. In further embodiments, treatment timelines or noise levels associated with specific operations can be updated based on readings from microphones and/or audio sensors, and updated volumes can be used in managing treatment.

According to some embodiments, the execution component 112 can include a timing component 116 that schedules start times for a course of treatment, specific operations, and/or limits execution of operations to pre-programmed time periods. In some examples, where operations are limited to specific time periods, the execution component 112 can be configured to override such limits based on real time analysis of sleep state and/or based on threshold noise levels. In other embodiments, the execution component 112 can also override scheduled start times based on patient sleep state determinations and/or threshold noise levels. The timing component 116 can also accept user input schedule information. In one example, a user can specify a start time for treatment and the timing component 116 can be configured to track time so that the execution component can start treatment according to user specific parameters.

User specified parameters can be input directly on a treatment system which can provide a graphical user interface or touch button interfaces for specifying start time. In one embodiment, the treatment controller 100 includes a graphical user interface component (GUI) 114. The GUI component 114 can generate and display user interfaces that accept user (e.g., the patient) specified timing for treatment execution. In other embodiments, the GUI component 114 can generate interfaces for users on remote devices (e.g., smart phones, tablets, etc.). In further embodiments, the GUI component 114 and/or communication interface 108 can accept user inputs entered on remote devices to set timing information.

The treatment controller 100 can also accept data from other applications (e.g., via the communication interface). In one embodiment, the sleep analysis component 110 can accept sleep state determinations from external applications (e.g., sleep manager programs and sleep manager sensors (e.g., in bed sensors, wearable sensors, etc.)), and use the received state in managing treatment execution.

In addition to controlling treatment based on sleep state and/or time, the treatment controller 100 can implement additional safety features based on sensor readings. In one embodiment, the treatment controller 100 can include a safety component 118 configured to monitor patient biologic/physiologic data. If the safety component detects an unsafe condition (e.g., too low heart rate, too low respiration rate, too high heart rate, too high respiration rate, too low/high temperature, etc.) the safety component 118 can initiate or suspend any treatment and generate audio and/or visual alarms. In some examples, the safety component can be configured to alert medical personnel (e.g. hospital, doctor's office, emergency room, urgent care clinic, etc.) where the unsafe condition could lead to a life threatening situation. Various thresholds can be set for each biological parameter (e.g., heart rate, respiration rate, temperature, etc.). For example, the safety component may be configured to generate an alert if the body temperature of the patient exceeds 100.4 degrees Fahrenheit.

Figure 2:
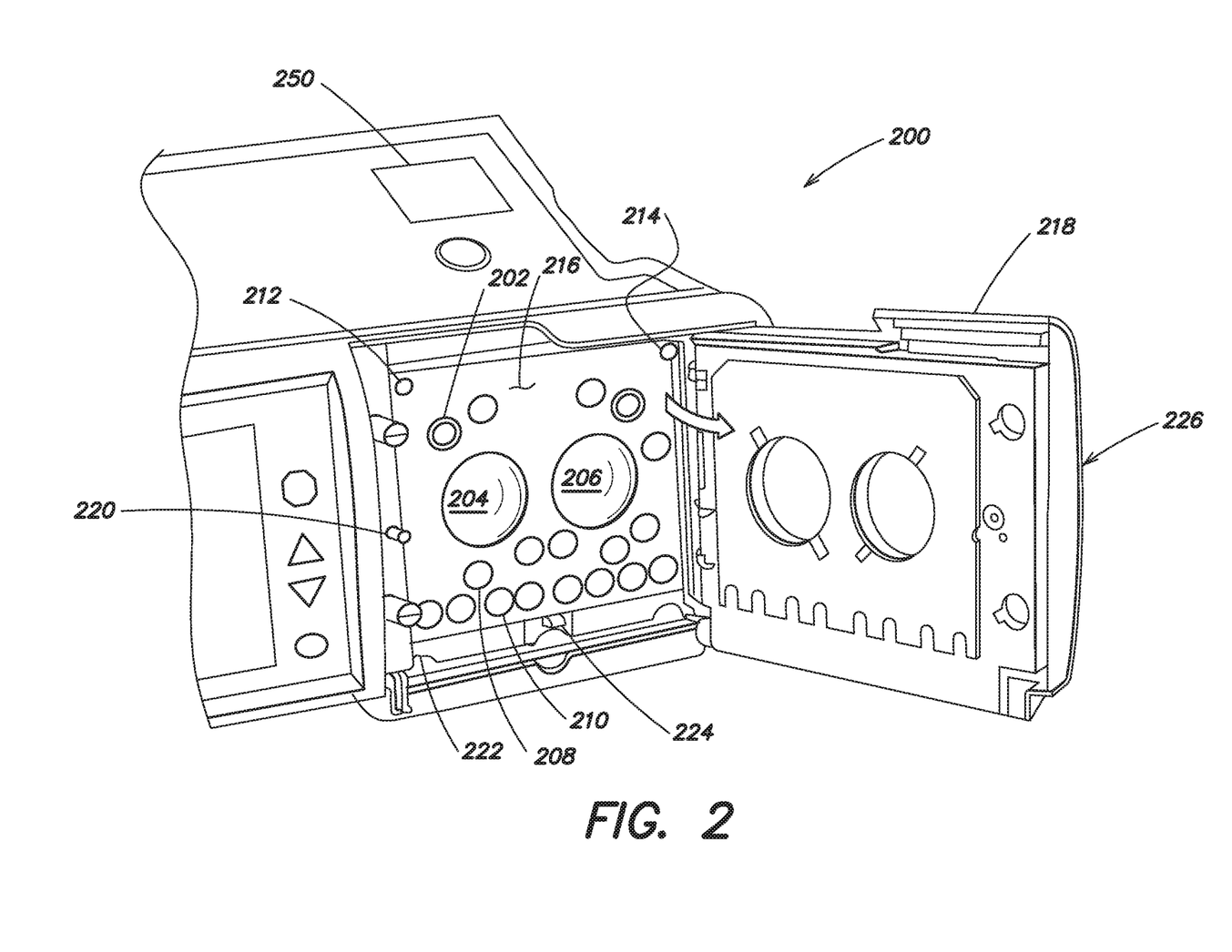
FIG. 2 is a block diagram of an example treatment system.

Shown in FIG. 2 is an example treatment system 200 that can incorporate a treatment controller 250 (e.g., treatment controller 100 illustrated in FIG. 1) or other system components (e.g., the control engine 104 or any of the components 108-118 illustrated in FIG. 1) to manage execution of treatment according to time and/or sleep state.

The treatment system 200 is configured to provide peritoneal dialysis. For example, the system manages delivery and removal of a dialysate solution to a peritoneal cavity of a patient. The dialysate is pumped into the patient's peritoneal cavity where the dialysate remains for a period time. While the dialysate is present in the peritoneal cavity, the dialysate absorbs contaminants and/or particulates from the patient's blood. Peritoneal dialysis uses the patient's peritoneum in the abdomen as a membrane across which fluids and dissolved substances (e.g., electrolytes, urea, glucose, albumin, osmotically active particles, and other small molecules) are exchanged from the blood.

The treatment system can include a pressure sensor 202 that provides readings on the fluid (e.g., dialysate). As discussed above, pressure readings can be taken continuously, intermittently, periodically, etc., to provide fluctuation data from which to extrapolate, for example, a patient heart rate and/or a patient respiration rate. It is appreciated that, in some examples, additional instruments may be employed to provide direct measurement of heart rate, respiration rate, and/or other biological characteristics pertinent to detecting a particular sleep state. The treatment system 200 operates pump heads 204 and 206 to move the fluid. The pump heads apply force to a cassette (not shown) that connect a fluid reservoir to a catheter at the patient's peritoneum. By operation of the pump heads 204 and 206, clean dialysate can be drawn from a fluid reservoir and introduced into the patient's peritoneum. Likewise, pump heads 204 and 206 can draw fluid from the patient's peritoneum into a fluid reservoir. Multiple reservoirs may be used including a clean fluid reservoir and a waste fluid reservoir. Operation of the pump heads in conjunction with valves (e.g., valves 208 and 210) configuration controls delivery or retrieval of fluid.

According to one embodiment, cassette guide pins 212 and 214 are present to ensure proper alignment of a cassette when inserted into the treatment system 200. A cassette pump plate 216 contains the pump mechanism and provides openings for the pump heads to operate on an inserted cassette. The door latch 218, door sensor 220, safety clamp 222, and cassette catch 224 are configured to ensure proper alignment and engagement with a cassette once inserted and once the cassette door 226 is closed.

The treatment controller 250 can be embedded in the treatment system 200, or can be coupled to the treatment system via a communication port (not shown) or wireless communication links. As an embedded component the treatment controller 250 can be directly connected to any one or more of the pressure sensor, door sensor, pump, pump heads, etc. The treatment controller 250 can communicate control signals or triggering voltages to the components of the treatment system. As discussed, various embodiments of the treatment controller (e.g., 100 and/or 250) can include wireless communication interfaces. The treatment controller can detect remote devices in proximity to determine if any remote sensors are available to augment any sensor data being used to evaluate the patient. In further embodiments, the treatment controller (e.g., 100 and/or 250) can detect and communicate with multiple remote devices to communicate with available sensors (e.g., smart phone microphones, video cameras, cameras, thermal imaging cameras, in bed sensors, sleep manager applications and sensors, web cameras, fitness sensors, stand-alone sensors, etc.) that may individually or collectively sense physiological data pertinent to detecting a sleep state in the patient.

In some examples, the treatment controller 250 can also manage treatment execution on the basis of co-sleeper sleep state. Each of the functions and sleep state analysis operations described above can be used to determine a sleep state for one or more co-sleepers, which can be used to trigger any noisy or loud operations of the treatment system based on both sleep states (e.g., patient sleep state and co-sleeper sleep state). Although a co-sleeper need not be receiving dialysis treatment, and therefore may not have certain data available (e.g., peritoneal pressure readings from the pressure sensor 202), physiological data with respect to the co-sleeper may be available from external sensors described above in the previous paragraph.

Figure 3:
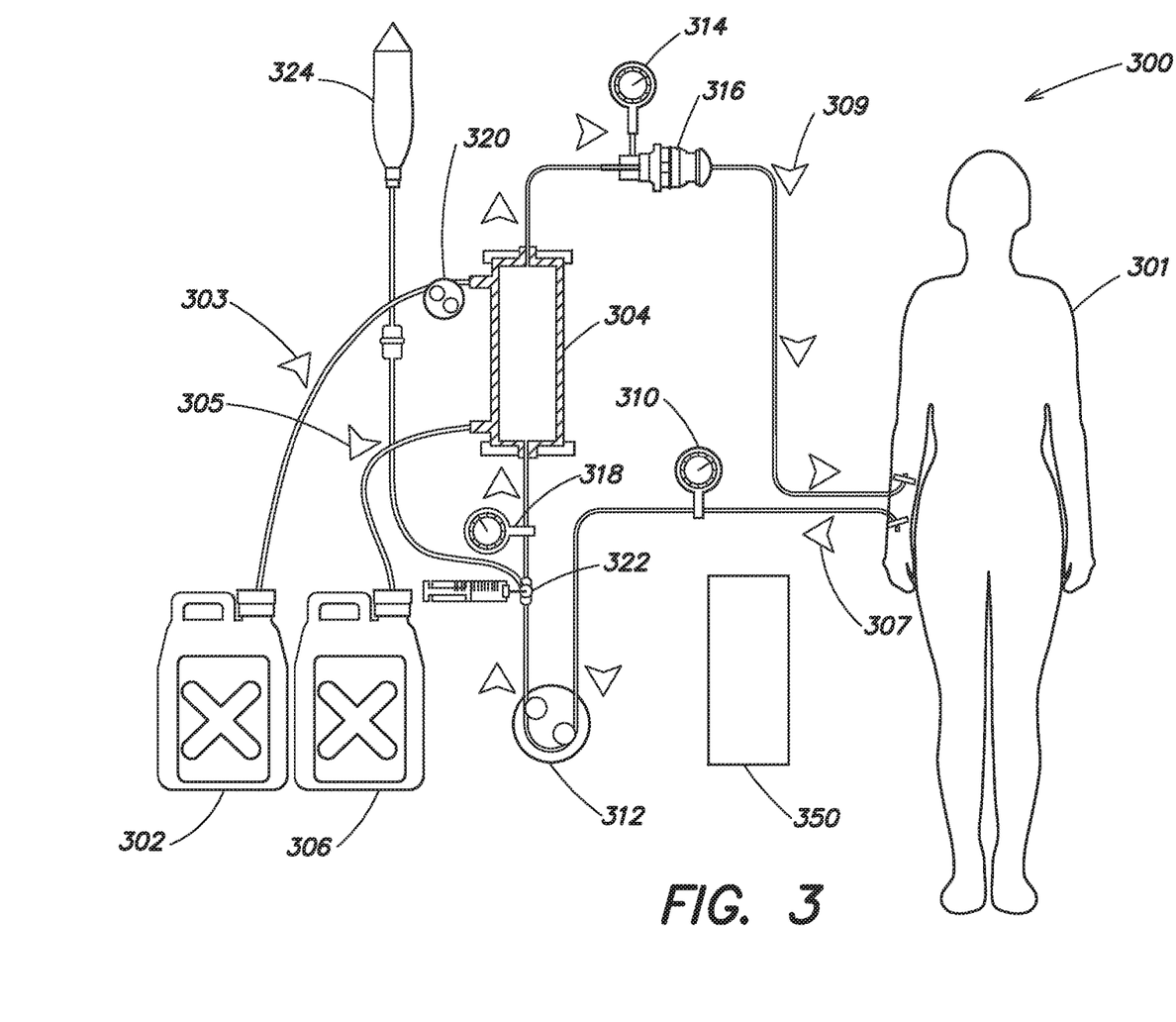
FIG. 3 is a block diagram of another example treatment system.

FIG. 3 is a diagram of another treatment system 300. Treatment system 300 is configured to provide hemodialysis treatment to a patient 301. Fluid reservoir 302 delivers clean dialysate to a dialyzer 304 at 303 and reservoir 306 receives spent dialysate once it has passed through the dialyzer 304 at 305. Hemodialysis treatment is characterized by filtering particulates and/or contaminates from patient blood through a patient external filtration device (e.g., the dialyzer 304). As the dialysate in passed through the dialyzer 304, so too unfiltered patient blood is passed into the dialyzer at 307 and filtered blood is returned to the patient at 309. Arterial pressure can be monitored via pressure sensor 310, inflow pressure monitored via sensor 318, and venous pressure monitored via pressure sensor 314. Air trap and detector 316 ensures that air is not introduced into patient blood as it is filtered and returned to the patient 301. The flow of blood and the flow of dialysate are controlled via respective pumps, (e.g., blood pump 312 and fluid pump 320). Heparin 322 (a blood thinner) may be used in conjunction with saline 324 to ensure blood clots do not form or occlude blood flow through the system.

According to some embodiments, the treatment system can include a treatment controller 350 (similar to, for example, 100, FIG. 1, 250, FIG. 2). The treatment controller 350 is configured to monitor blood pressure readings to identify fluctuations indicative of heart rate and/or respiration rate. Treatment controller 350 can also be connected to and/or communicate with additional sensors or sensor systems. The treatment controller can use any of the data available on the patient's biologic functions to determine sleep state or monitor safety parameters.

According to some embodiments, the operation of pumps 312 and 320 generate the greatest noise during treatment execution. Thus, treatment controller 350 can be specifically tailored to manage activation of pumps 312 and 320 based on determining the patient is entering or is in a deep sleep state. In further examples, other operations can generate noise in excess of thresholds, such as running enclosure cooling fans, and such operations can be limited to deep sleep states and/or scheduled to occur during deep sleep states.

Figure 4:
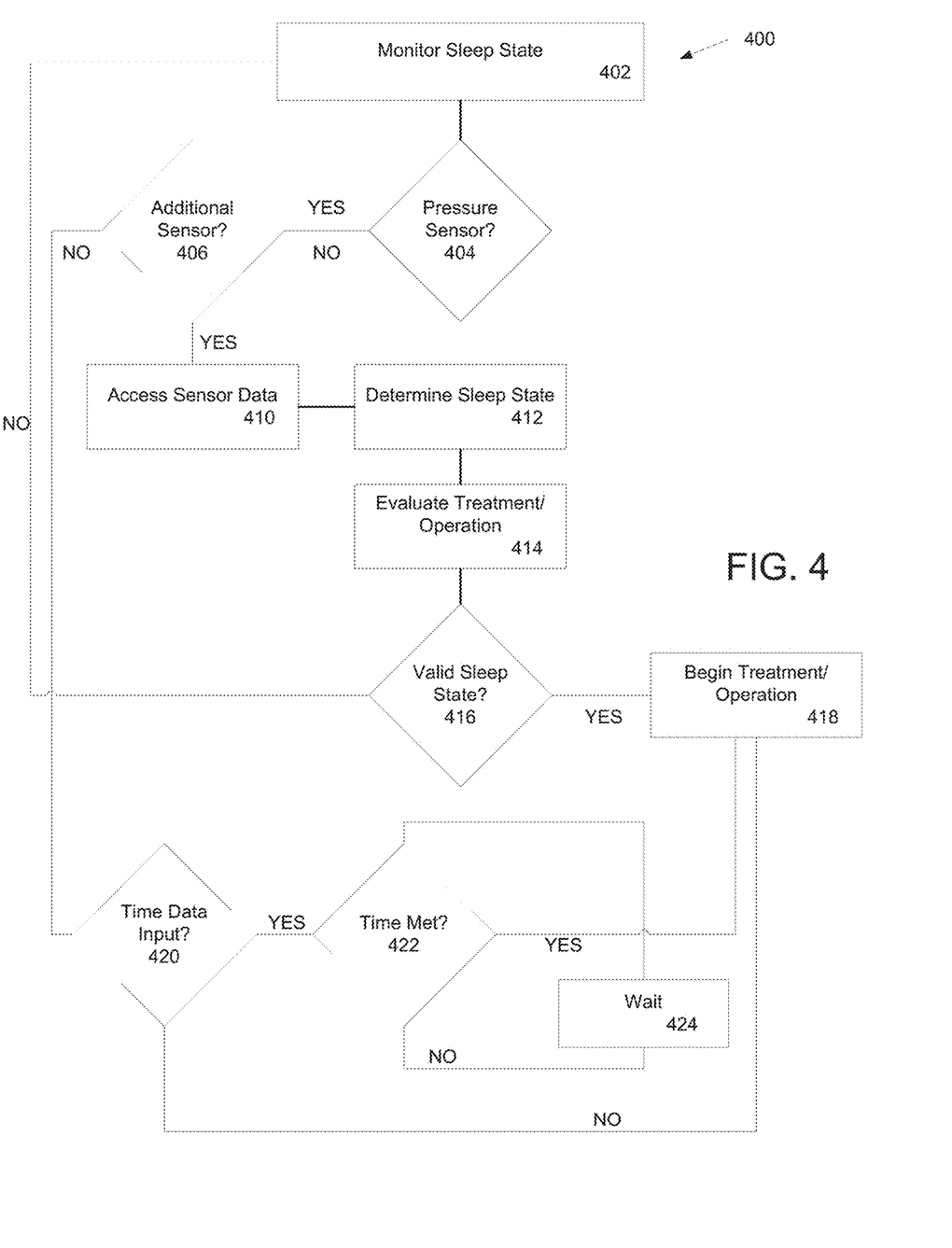
FIG. 4 is a flow diagram illustrating a process for controlling treatment execution responsive to sensor data.

FIG. 4 illustrates an example process 400 for managing treatment execution. Process 400 begins with monitoring sleep state at 402 for a patient having a scheduled treatment. In one example, process 400 is executed on a controller system or with a controller component that manages a treatment system (e.g., peritoneal dialysis system or hemodialysis system). The treatment system can be separate from the controller system or component. In some embodiments, the controller system or component can be an embedded system.

If a sensor is available 404 YES, the sensor data can be used to determined sleep state at 408. For example, a peritoneal dialysis system can include pressure sensors to monitor dialysate pressure in the patient's peritoneal cavity. In cases where multiple sensors are employed, sensor data from the additional sensors may be accessed to, for example, augment pressure sensor data or confirm pressure sensor data, and optionally, can be used instead of or without pressure sensor data. Available sensor data is accessed at 406 and is used to determine the patient's sleep state at 408. In some examples, the sensor data (e.g., pressure data) is analyzed to determine a heart rate and/or respiration rate for the patient. According to one embodiment, fluctuations in pressure readings can be correlated to heart beat and/or respiration rate. In further embodiments, large pressure changes can be correlated with patient movement. Using any one or more of heart rate, respiration rate, and/or patient movement, a patient sleep state can be determined at 408. The determination at 408 of the sleep state of the patient can be made by analyzing the sensor data to identify transitions between sleep states (e.g., transitions in sleep stages), by determining ranges of biologic readings that correspond to a specific sleep state, or with analysis of transitions and ranges of sensor readings.

As discussed above, determination of sleep state can be augmented by additional sensors (e.g., video, thermal imaging, respiration, heart rate, EEG, thermal, motion, audio, etc.). Determination of sleep state at 408 can include analysis of any available sensor data. In some embodiments, patients can link their mobile device (e.g., smart phones, tablets, fitness devices, etc.) or home computer systems (e.g., desktop, laptop, home security, etc.) to a treatment system, treatment controller, etc., to allow access to any attached sensor or application. In some examples, determination of sleep state at 408 can include image processing and/or image analysis of still photos, video, thermal imaging, etc.

At 410, process 400 can evaluate the scheduled treatment and/or specific operations that are executed as part of a course of treatment. In one example, evaluation at 410 includes analyzing an expected noise level associated with the treatment operation or course of treatment. At 412, the patient's sleep state is evaluated against the noise level to determine if a valid sleep state has been reached. For example, each sleep state (e.g, stage 1, stage 2, stage 3, REM sleep, etc.) can be associated with a noise threshold that is not expected to disturb the patient's sleep. So long as the noise level does not exceed the threshold for a given state execution of the treatment operation or beginning of the course of treatment can proceed at 414. In some embodiments, evaluation of the treatment/operation at 410 and determination of a valid sleep state at 412 can be executed together or as a single step to valid noise level against sleep state. In other embodiments, evaluation at 410 and 412 can be made based on projected noise levels, or real time noise levels, and can also be determined based on projected sleep states for a patient so that execution of a course of treatment or a treatment operation at 414 can be scheduled to coincide with projected sleep states, among other options.

If the patient is not in a valid sleep state for a given noise level 412 NO, process 400 can continue to monitor sleep state at 402 until a valid sleep state is identified and treatment begins. In some embodiments, starting a course of treatment or a treatment operation can be dependent on time inputs provided by a user (e.g., the patient). In one example, treatment execution is governed solely by time inputs (e.g., via 404 NO). Process 400 can proceed via 404 NO with a test for whether the user has input timing requirements at 416. If the user has input time data 416 YES, process 400 continues at 418 with a determination of whether the time requirement is met at 418. If met, 418 YES, treatment can begin or the treatment operation can be executed at 414. If not, 418 NO, then the process can enter a wait loop via 420 until the time is met at 418 YES and execution occurs at 418. In another execution, process 400 can proceed with treatment 414 if no time input data is available at 416 NO. According to one embodiment, treatment can proceed through 416 NO if time data was entered improperly. In another embodiment, treatment can also proceed via 402 NO, if no valid sleep state would be identified for a treatment period (e.g., one evening, defined sleep time, etc.).

According to another embodiment, steps 416-420 can be executed as a sub-process, which can occur prior to steps 402-414 (not shown). In such an embodiment, a user (e.g., patient) inputs timing requirements that may be a pre-cursor to any sleep state evaluation. For example, process 400 may first require satisfaction of user input requirements via steps 416-420 before validating the patient's sleep state by execution of steps 402-414.

Example Treatment Controller Implementation

As discussed above with regard to FIG. 1, a treatment controller 100 is provided that monitors a sleep cycle of a patient and preferentially operates various loud devices within a dialysis system at times when the patient is in REM sleep. FIG. 5 illustrates an example implementation of the treatment controller 100 illustrated in FIG. 1 suitable for use in, for example, hemodialysis and/or peritoneal dialysis systems as described above. As shown in FIG. 5, the treatment controller 500 includes a processor 502, data storage 504, a communication interface 506, a user interface 508, a sensor interface 510, and a therapy device interface 512. It is appreciated that the particular architecture shown in FIG. 5 is for illustration only and other architectures may be employed.

According to the example illustrated in FIG. 5, the processor 502 is coupled to the data storage 504, a communication interface 506, a user interface 508, a sensor interface 510, and a therapy device interface 512. The processor 502 performs a series of instructions that result in manipulated data which are stored in and retrieved from the data storage 504. According to a variety of examples, the processor 502 is a commercially available processor such as a processor manufactured by INTEL, AMD, MOTOROLA, and FREESCALE. However, the processor 502 may be any type of processor, multiprocessor or controller, whether commercially available or specially manufactured. For instance, according to one example, the processor 502 may include an MPC823 microprocessor manufactured by MOTOROLA.

In addition, in some examples, the processor 502 may be configured to execute an operating system. The operating system may provide platform services to application software, such as some examples of the sleep analysis component 110, the execution component 112, the timing component 116, and/or the safety component 118 as described above. These platform services may include inter-process and network communication, file system management and standard database manipulation. One or more of many operating systems may be used, and examples are not limited to any particular operating system or operating system characteristic. In some examples, the processor 502 may be configured to execute a real-time operating system (RTOS), such as RTLinux, or a non-real time operating system, such as BSD or GNU/Linux.

The data storage 504 includes a computer readable and writeable nonvolatile data storage medium configured to store non-transitory instructions and data. In addition, the data storage 504 includes processor memory that stores data during operation of the processor 504. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the data storage 504 may include executable programs or other code that can be executed by the processor 502. The instructions may be persistently stored as encoded signals, and the instructions may cause the processor 502 to perform the functions described herein. The data storage 504 may include information that is recorded, on or in, the medium, and this information may be processed by the processor 502 during execution of instructions. The data storage 504 may also include, for example, specification of data records for user timing requirements, noise levels produced during treatment, noise levels produced during respective treatment operation(s), timing for treatment and/or operations, historic sleep state information, historic sensor information, patient sleep state models. The medium may, for example, be optical disk, magnetic disk or flash memory, among others, and may be permanently affixed to, or removable from, the treatment controller 500.

As shown in FIG. 5, the medical device controller 500 includes several system interface components 506, 510, and 512. Each of these system interface components is configured to exchange data with one or more specialized devices that may be located within a housing of the dialysis treatment system or elsewhere. The components used by the interfaces 506, 510, and 512 may include hardware components, software components or a combination of both. Within each interface, these components physically and logically couple the treatment controller 500 to the specialized devices. This physical and logical coupling enables the treatment controller 500 to communicate with and, in some instances, power or control the operation of the specialized devices. These specialized devices may include, for example, various sensors, pumps, control valves, and computer networking devices.

According to various examples, the hardware and software components of the interfaces 506, 510, and 512 implement a variety of coupling and communication techniques. In some examples, the interfaces 506, 510, and 512 use leads, cables or other wired connectors as conduits to exchange data between the treatment controller 500 and specialized devices. In other examples, the interfaces 506, 510, and 512 communicate with specialized devices using wireless technologies such as radio frequency or infrared technology. The software components included in the interfaces 506, 510, and 512 enable the processor 502 to communicate with specialized devices. These software components may include elements such as objects, executable code, and populated data structures. Together, these software components provide software interfaces through which the processor 502 can exchange information with specialized devices. Moreover, in at least some examples where one or more specialized devices communicate using analog signals, the interfaces 506, 510, and 512 further include components configured to convert analog information into digital information, and vice versa, to enable the processor 502 to communicate with specialized devices.

As discussed above, the system interface components 506, 510, and 512 shown in the example of FIG. 5 support different types of specialized devices. The components of the sensor interface 510 couple the processor 502 to one or more sensors to, for example, gather information regarding a sleep state of the patient. For example, the sensor interface 510 may couple the processor 402 a pressures sensor as illustrated by pressure sensor 516. Other example sensors that may be coupled to the sensor interface 510 include a heart rate sensor, a respiration sensor, a temperature sensor, a video sensor, a thermal imaging sensor, an electroencephalogram sensor, a motion sensor, audio sensor, an accelerometer, or capacitance sensor. It is appreciated that the sensors may include sensors with varying sampling rates, including wireless sensors.

As illustrated in FIG. 5, the sensor interface 510 is coupled to a microphone 514. The microphone may be housed within, for example, the same treatment system that houses the treatment controller 500. As described above with reference to the treatment method of FIG. 4, the processor 502 may access the microphone via the sensor interface 510 to capture and record noise levels. In some examples, the processor 502 may record the noise levels in the data storage 504 and track the changes in the noise level when particular mechanical components are operating to, for example, identify mechanical component failures. For example, the processor 502 may identify that a pump has failed responsive to identifying a trend of increasing noise levels over time when the pump is operated.

In some examples, the components of the therapy delivery interface 512 couple one or more therapy delivery devices, such as pumps 518 and control valves 520 to the processor 502. It is appreciated that the functionality of the therapy delivery interface 502 may be incorporated into the sensor interface 510 to form a single interface coupled to the processor 502.

In addition, the components of the communication interface 506 couple the processor 502 to external systems via either a wired or wireless communication link. According to a variety of examples, the communication interface 506 supports a variety of standards and protocols, examples of which include USB, TCP/IP, ETHERNET, BLUETOOTH, ZIGBEE, CAN-bus, IP, IPV6, UDP, DTN, HTTP, HTTPS, FTP, SNMP, CDMA, NMEA and GSM. It is appreciated that the communication interface 506 of the treatment controller 500 may enable communication between other devices within a certain range.

In another embodiment, a treatment controller 500 can coordinate analysis of patient sleep state with external systems via the communication interface 506. For example, the treatment controller 500 may coordinate with other sensor systems, sleep management system, activity monitoring devices, fitness sensors. Example of sleep trackers include products produced by FITBIT, JAWBONE, SLEEPTRACKER, LARK, MELLON, ZEO, SLEEP CYCLE, SLEEP BOT, and SLEEP AS ANDRIOD, among other options. In some examples, the treatment controller 500 can evaluate the respective systems assessment of deep sleep versus light sleep and incorporate such assessments into a determination of the patient's sleep state. In some embodiments, the treatment controller 500 can be configured to identify light versus deep sleep and manage treatment using a two state model, as well as models with more sleep states.

The user interface 508 shown in FIG. 5 includes a combination of hardware and software components that allow the treatment controller 500 to communicate with an external entity, such as a patient or other user. These components may be configured to receive information from actions such as physical movement, verbal intonation, or thought processes. In addition, the components of the user interface 508 can provide information to external entities. Examples of the components that may be employed within the user interface 508 include keypads, buttons, microphones, touch screens, display screens, and speakers.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A dialysis treatment system comprising:
   at least one fluid conduit;
   at least one mechanical component coupled to the at least one fluid conduit; and
   a treatment controller configured to control operation of the at least one mechanical component to manage passage of a fluid through the at least one fluid conduit for a patient, wherein the treatment controller includes:
      a sleep state component configured to obtain current sleep state data for the patient; and
      an execution component configured to limit a loud operation of at least the at least one mechanical component at least by:
         based at least on the current sleep state data for the patient, projecting a future deep sleep state for the patient, and
         initiating a dialysis treatment during a sleep state of the patient that precedes the future deep sleep state, such that the loud operation of the at least one mechanical component during the dialysis treatment is expected to occur at a time during the future deep sleep state.

2. The system of claim 1, wherein the dialysis treatment system is a peritoneal dialysis treatment system, wherein the fluid is a dialysate, and wherein the treatment controller is configured to manage passage of dialysate for the patient at a peritoneal cavity of the patient.

3. The system of claim 1, wherein the dialysis treatment system is a hemodialysis treatment system, wherein the fluid is clean blood, and wherein the treatment controller is configured to manage delivery of the clean blood to the patient or dialysate to a dialyzer.

4. The system of claim 1, wherein the sleep state component is configured to obtain the current sleep state data for the patient at least by receiving physiologic data from one or more sensors.

5. The system of claim 1, further comprising a pressure sensor configured to monitor a pressure of the fluid, wherein the sleep state component is configured to determine at least one of a determined heart rate or a determined respiration rate responsive to analyzing pressure data provided by the pressure sensor.

6. The system of claim 5, wherein the sleep state component is configured to determine the determined heart rate or the determined respiration rate responsive to identifying fluctuations in pressure data provided by the pressure sensor.

7. The system of claim 5, wherein the sleep state component is configured to correlate the determined heart rate or the determined respiration rate to a sleep state stage of the patient.

8. The system of claim 1, wherein the treatment controller is configured to project a course of the dialysis treatment to determine a timing for the loud operation of the at least one mechanical component, based at least on the loud operation of the at least one mechanical component being above a predefined noise threshold.

9. The system of claim 1, further comprising a database and data records defining expected noise levels associated with each dialysis treatment operation performed by the dialysis treatment system.

10. The system of claim 1, further comprising an audio sensor to detect noise levels, wherein the treatment controller is configured to:
monitor the noise levels; and
manage treatment execution responsive to the noise levels.

11. The system of claim 10, wherein the treatment controller stores noise levels associated with respective treatment operations in a database.

12. The system of claim 11, wherein the treatment controller is further configured to compare detected noise levels to stored noise levels in the database, and based on the comparison, detect a failure in the at least one mechanical component.

13. The system of claim 1, wherein the sleep state component is configured to store historical sleep state data for the patient.

14. The system of claim 13, wherein projecting the future deep sleep state for the patient is further based on analyzing the historical sleep state data for the patient.

15. The system of claim 1, wherein the execution component is configured to estimate a plurality of times associated with a plurality of treatment operations over a course of dialysis treatment.

16. The system of claim 1, further comprising a timer component configured to accept user input of timing information.

17. The system of claim 16, wherein the execution component is configured to manage execution of the dialysis treatment based on the user input timing information.

18. The system of claim 17, wherein the execution component is configured to limit treatment operations performed during the dialysis treatment that exceed a pre-defined noise threshold until any requirement specified by the timing information is satisfied.

19. The system of claim 17, wherein the user input timing information defines one or more sleep states for the patient.

20. The system of claim 19, wherein upon satisfying a condition specified by the timing information, the system is configured to assign a sleep state from the one or more sleep states to the patient.

21. The system of claim 1, further comprising one or more sensors for directly monitoring at least the patient.

22. The system of claim 21, wherein the one or more sensors include any one or more of a heart rate sensor, a respiration sensor, a temperature sensor, a video sensor, a thermal imaging sensor, an electroencephalogram sensor, a motion sensor, an audio sensor, an accelerometer, or a capacitance sensor.

23. The system of claim 22, further comprising a communication device coupled to the treatment controller and wherein the treatment controller is configured to establish a communication link via the communication device to an external device including at least one of the one or more sensors.

24. The system of claim 23, wherein the treatment controller is configured to receive sensor data via the communication link.

25. The system of claim 22, wherein the sleep state component is configured to analyze the data from the one or more sensors to determine a current sleep state stage of the patient.

26. The system of claim 1, wherein the sleep component is further configured to determine a sleep state stage for a co-sleeper other than the patient.

27. The system of claim 26, wherein the sleep state component is configured to identify the co-sleeper responsive to one or more of analyzing sensor data and/or receiving user input regarding a number of sleepers.

28. The system of claim 26, wherein the execution component is configured to harmonize treatment execution such that treatment operations having a noise level in excess of a threshold are executed during time periods that both the patient and co-sleeper are simultaneously in a deep sleep state.

29. The system of claim 1, further comprising a safety component configured to monitor sensor data received from one or more sensors.

30. The system of claim 29, wherein the safety component is configured to correlate sensor data from the one or more sensors to one or more of a heart rate of the patient and/or a respiration rate of the patient.

31. The system of claim 30, wherein the safety component is configured to monitor one or more of the heart rate and/or the respiration rate to determine a safe range, and to terminate treatment or alarm responsive to values outside of the safe range.

32. The system of claim 1, wherein the execution component is further configured to limit the operation of the at least one mechanical component at least by:
(a) determining, based at least on historical sleep data associated with the patient, that noise above a particular noise level disturbs sleep for the patient;

(b) determining that the loud operation of the at least one mechanical component exceeds the particular noise level; and based at least on (a) and (b), determining a time for initiating the dialysis treatment such that the loud operation of the at least one mechanical component during the dialysis treatment is expected to occur at a time during the future deep sleep state.

33. The system of claim 1, wherein the execution component is further configured to limit the operation of the at least one mechanical component at least by:

(a) determining, based at least on data gathered by a noise sensor during a prior dialysis treatment, an actual noise level associated with the at least one mechanical component;

(b) determining that the actual noise level exceeds a threshold noise level; and based at least on (a) and (b), determining a time for initiating the dialysis treatment such that the loud operation of the at least one mechanical component during the dialysis treatment is expected to occur at a time during the future deep sleep state.

34. The system of claim 1, wherein the loud operation of the at least one mechanical component is a loudest operation among a plurality of operations performed by the at least one mechanical component during the dialysis treatment.

35. The system of claim 1, wherein during the dialysis treatment, the at least one mechanical component also performs at least one operation coinciding with at least one sleep state for the patient other than the future deep sleep state.

36. A method for operating a dialysis treatment system, the method comprising:

controlling, by a treatment controller, operation of at least one mechanical component coupled to at least one fluid conduit to manage passage of fluid through the at least one conduit for a patient to perform dialysis, at least by:

obtaining, by a sleep state component of the treatment controller, current sleep state data for the patient; and limiting, by an execution component of the treatment controller, a loud operation of at least the at least one mechanical component at least by:

based at least on the current sleep state data for the patient, projecting a future deep sleep state for the patient, and initiating a dialysis treatment during a sleep state of the patient that precedes the future deep sleep state, such that the loud operation of the at least one mechanical component during the dialysis treatment is expected to occur at a time during the future deep sleep state.

37. The method of claim 36, wherein the at least one fluid conduit and the at least one mechanical component are components of a peritoneal dialysis subsystem, and the method further comprises managing, by the treatment controller, at least passage of dialysate for the patient at a peritoneal cavity of the patient.

38. The method of claim 36, wherein the at least one fluid conduit and the at least one mechanical component are components of a hemodialysis subsystem, and the method further comprises managing, by the treatment controller, at least delivery of clean blood to the patient or dialysate to a dialyzer.

39. The method of claim 36, wherein obtaining the current sleep state data for the patient includes receiving physiologic data from one or more sensors.

40. The method of claim 36, wherein obtaining the current sleep state data for the patient includes monitoring a pressure of the fluid.

41. The method of claim 40, wherein obtaining the current sleep state data for the patient includes determining at least one of a heart rate or a respiration rate responsive to analyzing pressure data provided by a pressure sensor.

42. The method of claim 41, wherein determining the heart rate or the respiration rate is performed responsive to identifying fluctuations in the pressure data provided by the pressure sensor.

43. The method of claim 41, further comprising correlating the heart rate or the respiration rate to a sleep state for the patient.

44. The method of claim 36, wherein the loud operation is a treatment operation exceeding a predefined noise threshold according to time or sleep state.

45. The method of claim 44, further comprising storing one or more data records defining expected noise levels associated with each dialysis treatment operation performed by the dialysis treatment system.

46. The method of claim 44, further comprising monitoring real time noise levels by audio sensors.

47. The method of claim 46, further comprising managing treatment execution responsive to the real time noise levels.

48. The method of claim 47, further comprising storing the real time noise levels associated with respective treatment operations in a database.

49. The method of claim 36, further comprising storing historical sleep state data for the patient.

50. The method of claim 49, wherein projecting the future deep sleep state for the patient is further based on analyzing the historical sleep state data.

51. The method of claim 36, further comprising accepting user input of timing information.

52. The method of claim 51, further comprising managing execution of dialysis treatment based on the user input timing information.

53. The method of claim 52, further comprising limiting treatment operations performed during dialysis treatment that exceed a pre-defined noise threshold until any requirement specified by the timing information is satisfied.

54. The method of claim 52, wherein the user input timing information defines a sleep state for the patient.

55. The method of claim 54, further comprising determining satisfaction of a condition specified by the timing information, and assigning a sleep state to the patient.

56. The method of claim 36, further comprising communicating with one or more sensors for directly monitoring at least the patient.

57. The method of claim 56, wherein the one or more sensors include any one or more of a heart rate sensor, a respiration sensor, a temperature sensor, a video sensor, a thermal imaging sensor, an electroencephalogram sensor, a motion sensor, an audio sensor, an accelerometer, or a capacitance sensor.

58. The method of claim 57, further comprising establishing a communication link to a mobile device including at least one of the one or more sensors.

59. The method of claim 58, further comprising requesting or receiving sensor data through the mobile device.

60. The method of claim 57, further comprising analyzing the data from the one or more sensors to determine a sleep state of the patient.

61. The method of claim 57, further comprising identifying one or more co-sleepers responsive to analyzing sensor data or receiving user input regarding a number of sleepers.

62. The method of claim 61, further comprising determining a sleep state for a co-sleeper.

63. The method of claim 62, further comprising harmonizing treatment execution such that treatment operations having a noise level in excess of a threshold are executed during time periods that both the patient and co-sleeper are in deep sleep states.

64. The method of claim 36, further comprising monitoring sensor data received from one or more sensors for safety parameters.

65. The method of claim 64, further comprising correlating pressure data to a heart rate or a respiration rate.

66. The method of claim 65, further comprising monitoring the heart rate or the respiration rate, determining safe ranges, and terminating treatment or generating one or more alarms responsive to values outside of the safe ranges.

* * * * *